(12) United States Patent
Takemura et al.

(10) Patent No.: US 11,459,537 B2
(45) Date of Patent: Oct. 4, 2022

(54) SENSOR DEVICE AND DETECTION APPARATUS

(71) Applicant: Sony Corporation, Tokyo (JP)

(72) Inventors: Ichiro Takemura, Kanagawa (JP);
Daisuke Yamaguchi, Kanagawa (JP);
Yoshio Goto, Kanagawa (JP); Kyohei Yoshimitsu, Tokyo (JP)

(73) Assignee: Sony Corporation, Tokyo (JP)

( * ) Notice: Subject to any disclaimer, the term of this patent is extended or adjusted under 35 U.S.C. 154(b) by 12 days.

(21) Appl. No.: 16/632,111

(22) PCT Filed: Apr. 19, 2018

(86) PCT No.: PCT/JP2018/016101
§ 371 (c)(1),
(2) Date: Jan. 17, 2020

(87) PCT Pub. No.: WO2019/017030
PCT Pub. Date: Jan. 24, 2019

(65) Prior Publication Data
US 2020/0172849 A1 Jun. 4, 2020

(30) Foreign Application Priority Data
Jul. 19, 2017 (JP) .............................. JP2017-140317

(51) Int. Cl.
*C12M 1/00* (2006.01)
*C12M 1/12* (2006.01)
*G01N 21/75* (2006.01)

(52) U.S. Cl.
CPC ............ *C12M 41/06* (2013.01); *C12M 25/00* (2013.01); *C12M 31/00* (2013.01); *G01N 21/75* (2013.01)

(58) Field of Classification Search
CPC ...... C12M 21/75; C12M 25/00; C12M 31/00; C12M 41/06; C12M 41/36; C12M 41/46;
(Continued)

(56) References Cited

U.S. PATENT DOCUMENTS

2002/0173040 A1* 11/2002 Potyrailo ............... G01N 33/28
436/2
2011/0275106 A1* 11/2011 Ichiki .................. G01N 33/5008
435/29

(Continued)

FOREIGN PATENT DOCUMENTS

JP  2012-196198 A  10/2012
WO  2009/157211  12/2009
(Continued)

OTHER PUBLICATIONS

Zhu, H., et al., Micro-patterning and characterization of PHEMA-co-PAM-based optical chemical sensors for lab-on-a-chip applications, Sens Actuators B Chem. Oct. 1, 2012; 173: 817-823. (14 pages).

*Primary Examiner* — William H. Beisner
*Assistant Examiner* — Danielle B Henkel
(74) *Attorney, Agent, or Firm* — K&L Gates LLP

(57) ABSTRACT

A sensor device according to the present technology includes a stack sensor. The stack sensor includes a first sensor layer and a second sensor layer. The first sensor layer has, as a detection target, a first substrate in a culture solution, the first substrate being changed in accordance with a change in a state of a cell. The second sensor layer has, as a detection target, a second substrate in the culture solution and is provided on the first sensor layer, the second substrate being changed in accordance with the change in the state.

5 Claims, 10 Drawing Sheets

(58) Field of Classification Search
CPC .................. G01N 21/77; G01N 21/78; G01N 2021/7786; G01N 21/75
See application file for complete search history.

(56) References Cited

U.S. PATENT DOCUMENTS

| | | | |
|---|---|---|---|
| 2012/0186997 A1* | 7/2012 | Li | C12Q 1/005 205/778 |
| 2015/0147231 A1* | 5/2015 | Tscherner | G01N 21/7703 422/82.07 |
| 2017/0240949 A1* | 8/2017 | Brutinel | C12Q 1/06 |

FOREIGN PATENT DOCUMENTS

| WO | 2009/157211 A1 | 12/2009 | |
|---|---|---|---|
| WO | 2017/073728 A1 | 5/2017 | |
| WO | WO-2017073728 A1 * | 5/2017 | ............. G01N 21/64 |
| WO | 2017-073728 | 9/2018 | |

* cited by examiner

SENSOR DEVICE AND DETECTION APPARATUS

TECHNICAL FIELD

The present technology relates to a sensor device and a detection apparatus that detect biological activity of a cultured cell.

BACKGROUND ART

Various cell experiments have been carried out in medical and drug discovery research sites from the past. In particular, in research for detecting a change in the state of a cultured cell by applying an external stimulus to the cultured cell, a method of measuring a substrate in a culture solution, which is changed in accordance with a change in the state of the cultured cell, is intensively studied.

For example, Patent Literature 1 describes a technology for providing, in a microchamber, a sensor layer in which probe molecules that react with a substrate in a culture solution are embedded in a culture substrate and detecting a change in the substrate that has been transmitted through the sensor layer.

Further, Non-Patent Literature 1 describes a technology for detecting changes in a plurality of substrates using a sensor array in which patterns of a sensor layer that responds to the pH of a culture solution and a sensor layer that responds to oxygen are individually formed by photolithography.

CITATION LIST

Patent Literature

Patent Literature 1: Japanese Patent Application No. 2010-517771

Non-Patent Literature

Non-Patent Literature 1: Haixin Zhu, Xianfeng Zhou, Fengyu Su, Yanqing Tian, Shashanka Ashili, Mark R. Holl, Deirdre R. Meldrum, "Micro-patterning and characterization of PHEMA-co-PAM-based optical chemical sensors for lab-on-a-chip applications" Sensors and Actuators B 173 (2012) 817-823

DISCLOSURE OF INVENTION

Technical Problem

However, in existing sensor devices including those in Patent Literature 1 or Non-Patent Literature 1, it is necessary to install the corresponding sensor layer including a plurality of sensor layers in the horizontal direction in order to detect changes in a plurality of substrates in a culture solution. This causes a problem that an apparatus configuration becomes larger.

In view of the circumstances as described above, it is an object of the present technology to provide a sensor device and a detection apparatus that are capable of detecting changes in a plurality of substrates in a culture solution and have a compact apparatus configuration.

Solution to Problem

In order to achieve the above-mentioned object, a sensor device according to an embodiment of the present technology includes a stack sensor.

The stack sensor includes a first sensor layer and a second sensor layer.

The first sensor layer has, as a detection target, a first substrate in a culture solution, the first substrate being changed in accordance with a change in a state of a cell.

The second sensor layer has, as a detection target, a second substrate in the culture solution and is provided on the first sensor layer, the second substrate being changed in accordance with the change in the state.

In accordance with the above-mentioned configuration, the second sensor layer is staked on the first sensor layer. As a result, the sensor device can be made compact, and it is possible to miniaturize various apparatuses including this sensor device and simplify them.

The first sensor layer may contain a first optically active substance that reacts with the first substrate, and the second sensor layer may contain a second optically active substance that reacts with the second substrate and has a first main surface to be in contact with the first sensor layer and a second main surface to be in contact with the cell.

The second sensor layer may have a transmittance of the first substrate higher than that of the first sensor layer.

As a result, it is possible to detect the plurality of substrates in the culture solution with the sensor device alone.

The second sensor layer may have an opening leading to the first sensor layer.

As a result, it is possible to detect the plurality of substrates in the culture solution with the sensor device alone.

The first sensor layer may contain a first optically active substance that reacts with oxygen being the first substrate, and the second sensor layer may contain a second optically active substance that reacts with a hydrogen ion being the second substrate.

The first sensor layer may contain platinum porphyrin as the first optically active substance, and the second sensor layer may contain fluorescein as the second optically active substance.

The sensor device may further include a support substrate that supports the stack sensor.

The first sensor layer may have a third main surface to be in contact with the support substrate and a fourth main surface to be in contact with the second sensor layer, and has solubility in the culture solution higher than that of the second sensor layer.

As a result, since the first sensor layer is sandwiched between the second sensor layer having low solubility in the culture solution and the support substrate, the optically active substance contained in the first sensor layer is prevented from being eluted in the culture solution. Therefore, the cell is prevented from being damaged by the optically active substance leaked into the culture solution.

The stack sensor may include a plurality of stack sensors provided the support substrate at predetermined intervals.

As a result, it is possible to detect the plurality of substrates in the culture solution with the sensor device alone.

The sensor device may further include a third sensor layer that is aligned with the first sensor layer.

In order to achieve the above-mentioned object, a detection apparatus according to an embodiment of the present technology includes: a sensor device; a light source; and a detection unit.

The sensor device includes a stack sensor and is disposed on an inner surface of a culture container, the stack sensor including a first sensor layer that has, as a detection target, a first substrate in a culture solution, the first substrate being changed in accordance with a change in a state of a cell, and a second sensor layer that has, as a detection target, a second substrate in the culture solution and is provided on the first sensor layer, the second substrate being changed in accordance with the change in the state.

The light source applies light to the stack sensor.

The detection unit detects light that has been transmitted through the stack sensor.

Advantageous Effects of Invention

As described above, in accordance with the present technology, it is possible to provide a sensor device and a detection apparatus that are capable of detecting changes in a plurality of substrates in a culture solution and have a compact apparatus configuration.

It should be noted that the above-mentioned effect is not necessarily limitative, and any effect described in the present specification or other effects that can be grasped from the present specification may be exerted in addition to or instead of the above-mentioned effect.

MODE(S) FOR CARRYING OUT THE INVENTION

Hereinafter, an embodiment of the present technology will be described with reference to the drawings.

[Configuration of Detection Apparatus]

Figure 1:
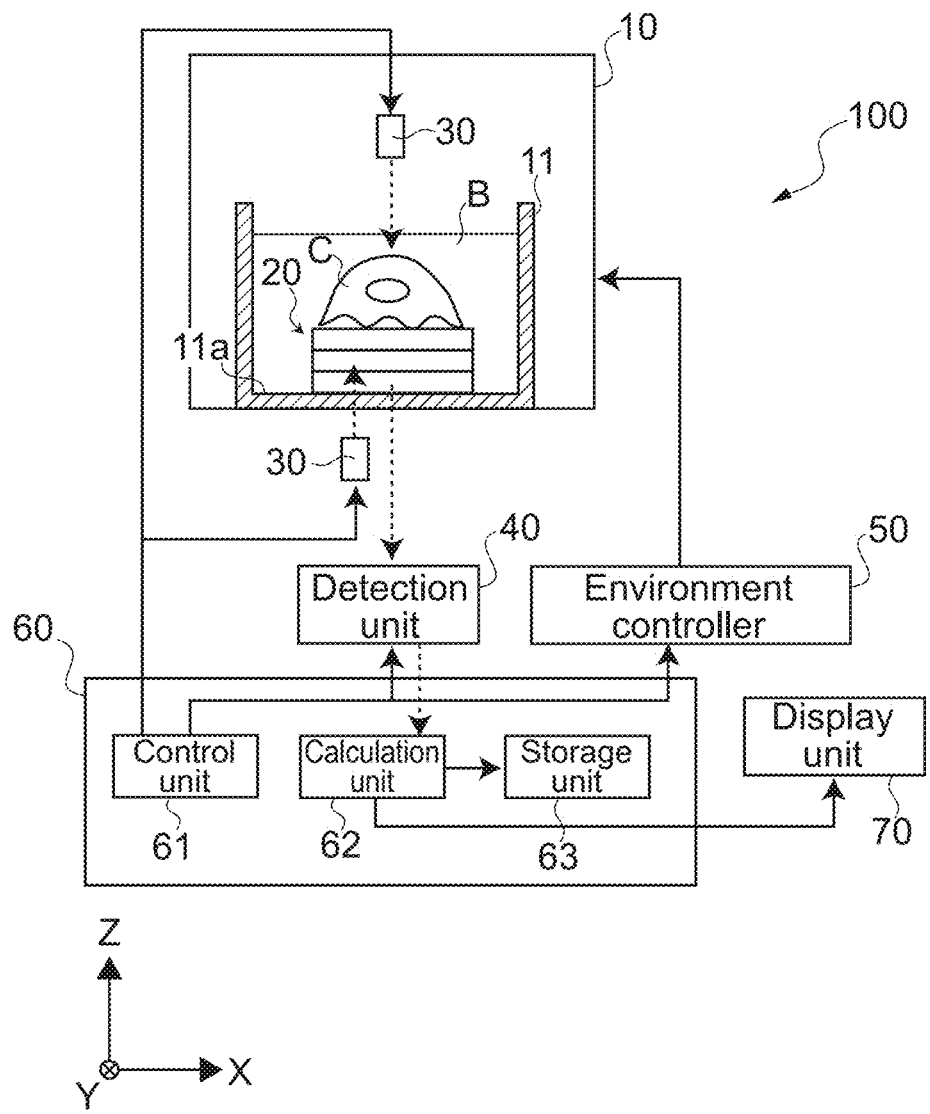
FIG. 1 is a schematic diagram showing a configuration example of a detection apparatus according to a first embodiment of the present technology.

FIG. 1 is a schematic diagram showing a configuration example of a detection apparatus 100 according to an embodiment of the present technology. As shown in FIG. 1, the detection apparatus 100 includes a sensor device 20, a light source 30, and a detection unit 40. Note that an X axis, a Y axis, and a Z axis in FIG. 1 represent three axis directions orthogonal to each other, and are common to all the figures in the present specification.

As shown in FIG. 1, the sensor device 20 is installed on a bottom surface 11$a$ (inner surface) of a culture container 11 and adhered to a cell C. The sensor device 20 is configured to be capable of detecting a change in a substrate in a culture solution B, which is changed in accordance with a change in the state of the cell C. This substrate is a substance secreted into the culture solution B when the cell C receives an external stimulus such as light, or a substance (environmental factor) in the culture solution B, which is to be changed in accordance with the change in the state of the cell C.

Examples of the above-mentioned substrate include oxygen, a reactive oxygen species, nitric oxide, glucose, lactate, pyruvate, cortisol, creatinine, urea, sodium, magnesium, calcium, potassium, vasopressin, a hormone (e.g., luteinizing hormone), a hydrogen ion, a cytokine, a chemokine, an eicosanoid, insulin, leptin, a small molecule drug, ethanol, myoglobin, a nucleic acid (RNA, DNA), a fragment of the cell C, a polypeptide, and a single amino acid.

Figure 3:
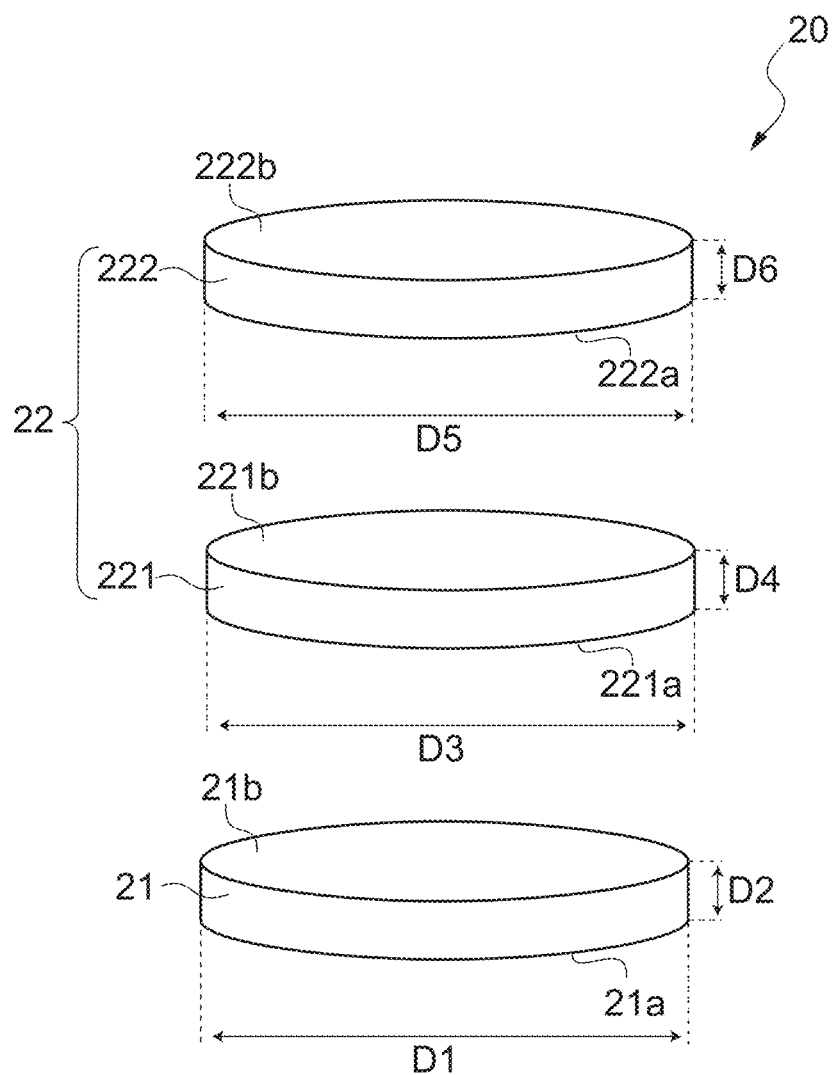
FIG. 3 is an exploded perspective view showing a configuration example of a sensor device according to the above-mentioned embodiment.

The sensor device 20 includes a support substrate 21 and a stack sensor 22 (see FIG. 3). The stack sensor 22 is formed of an arbitrary cell scaffold material (matrix material) that is adhered to the cell C in the culture solution B and contains an optically active substance (e.g., a dye). As a result, the stack sensor 22 functions as a scaffold when the cell C is cultured.

Examples of the above-mentioned cell scaffold material include a synthetic polymer, a naturally occurring matrix material, and a mixture thereof.

Examples of the synthetic polymer include polyethylene glycol (PEG), 2-hydroxyethyl methacrylate (HEMA), silicone rubber, poly (ε-caprolactam) dimethyl acrylate, a polysulfone, (poly) methyl methacrylate (PMMA), soluble polytetrafluoroethylene-AF, (Poly) ethylenetetraphthalate (PET, Dacron), nylon, polyvinyl alcohol, polyacrylamide, polystyrene, polyurethane, and a mixture thereof.

Examples of the naturally occurring matrix material include a fibrillar or globular protein, a complex carbohydrate, glycosaminoglycan, an extracellular matrix, or a mixture thereof.

Further, the cell scaffold material constituting the stack sensor 22 may contain any of all kinds of collagen, elastin, hyaluronic acid, arginic acid, desmin, versican, SPARC (osteonectin), osteopontin, thrombospondin-1, thrombospondin-2, fibrin, fibronectin, vitronectin, albumin, chitosan, or the like.

Further, in this embodiment, the stack sensor 22 may be formed of a hydrogel. Examples of the hydrogel include silicone hydrogel, siloxane gel, tetra-PEG (polyethylene glycol) gel, NVP (N-vinylpyrrolidone) gel, and MAA (methacrylic acid) gel.

In addition, the optically active substance contained in the cell scaffold material constituting the stack sensor 22 is, for example, a substance whose optical properties are changed in accordance with oxygen or a hydrogen ion in a culture solution, the temperature of the culture solution, or the like. Examples thereof include ethidium bromide, nile blue, luciferin, Lumazine protein, fluorescein, SYBR green, cyanine, a merocyanine, pyranine, perylene, umbelliferone, stilbene, coumarin, green fluorescent protein, rubrene, a porphyrin metal complex, a phthalocyanine metal complex, and DAPI (4',6-diamidino-2-phenylindole).

As shown in FIG. 1, two light sources 30 are disposed, i.e., one of them is disposed on the side of the bottom surface 11a of the culture container 11 and the other is disposed above the cell C. The light source 30 is configured to be capable of applying light of various wavelengths to the cell C and the sensor device 20. The type of the light source 30 is not particularly limited. However, for example, an LED (light emitting diode) light source, a semiconductor laser, or the like is adopted.

Note that the light source 30 of the detection apparatus 100 may be provided only either on the side of the bottom surface 11a of the culture container 11 or above the cell C as necessary. Three or more light sources 30 may be provided at different positions as long as they are capable of applying light to the stack sensor 22 at the positions.

The light source 30 typically emits excitation light for exciting the optically active substance contained in the stack sensor 22, and the wavelength of the excitation light is, for example, not less than 280 nm and not more than 800 nm. The light source 30 in this embodiment may be a monochromatic light source, or a light source obtained by combining a plurality of light sources.

Further, the light emission of the light source 30 may be continued for a predetermined time or may be pulse-lit in an arbitrary pattern. Further, a plurality of light sources 30 having the same or different wavelength characteristics may be sequentially caused to emit light, or the plurality of light sources 30 may be simultaneously caused to emit light.

The detection unit 40 is configured to be capable of detecting light modulated by light emitted from the light source 30 being transmitted through the sensor device 20. The detection unit 40 is typically a light reception sensor that detects luminescence corresponding to the change in the substrate in the culture solution B, which has been emitted from the sensor device 20. The change in the substrate has occurred by the application, to the sensor device 20, of the excitation light for exciting the optically active substance that has reacted with the substrate in the culture solution B.

The detection unit 40 receives luminescence from the sensor device 20, and outputs an electrical signal corresponding to the intensity of the luminescence to a calculation unit 62 described below. Examples of the detection unit 40 include an image sensor such as a CCD (Charge Coupled Device) sensor and a CMOS (Complementary Metal-Oxide Semiconductor) sensor.

Note that the above-mentioned luminescence refers to light (fluorescence, phosphorescence, or the like) that does not involve heat when the optically active substance that has reacted with the substrate is excited by absorbing light energy and returns to the ground state. The same applies also to the following description.

As shown in FIG. 1, the detection apparatus 100 according to this embodiment further includes an incubator 10, an environment controller 50, an information processing apparatus 60, and a display unit 70.

The incubator 10 is a culture device that houses the culture container 11 and has a function of keeping the temperature, humidity, and the like inside thereof constant. The incubator 10 is configured to allow an arbitrary gas to flow thereinto. The type of this gas is not particularly limited. However, the gas is, for example, nitrogen, oxygen, or carbon dioxide.

Figure 2:
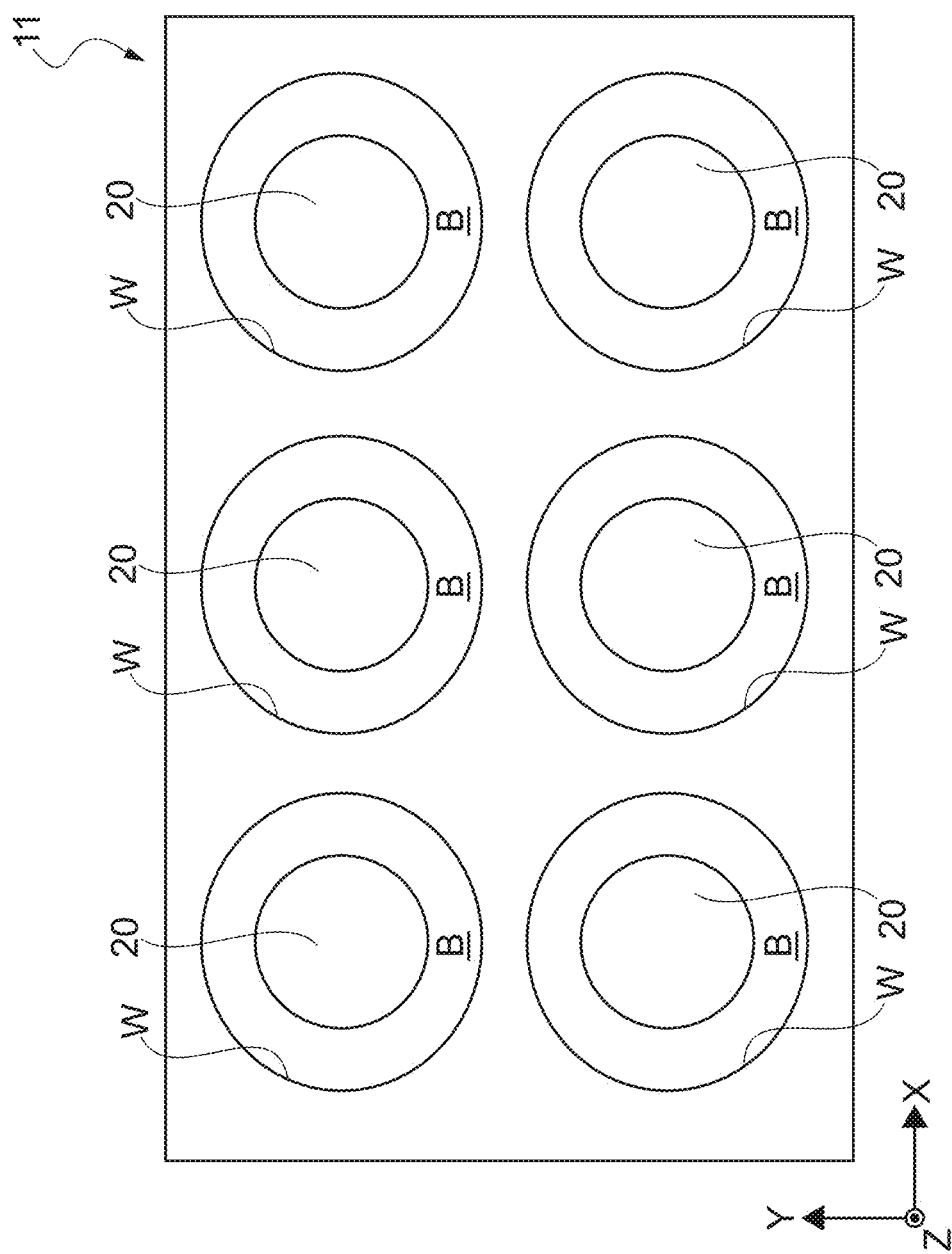
FIG. 2 is a plan view of a culture container in the above-mentioned embodiment.

FIG. 2 is a plan view of the culture container 11. The culture container 11 is, for example, a well plate provided with a plurality of wells W each housing the sensor device 20 adhered to the cell C.

As shown in FIG. 2, three wells W are formed in the Y axis direction and two wells W are formed in the X axis direction in the culture container 11, and one sensor device 20 is housed in each well W. Note that illustration of the cell C is omitted in FIG. 2.

In addition to housing the sensor device 20, the culture solution B and oil (not shown) are injected into the well W of the culture container 11. This oil has a function of suppressing evaporation of the culture solution B by coating the culture solution B.

The material forming the culture container 11 is not particularly limited, but is, for example, a transparent body through which light emitted from the light source 30 is transmitted, which is formed of an inorganic material such as glass and silicon, or an organic material such as a polystyrene resin, a polyethylene resin, a polypropylene resin, an ABS resin, nylon, an acrylic resin, a fluoropolymer, a polycarbonate resin, a polyurethane resin, a methylpentene resin, a phenolic resin, a melamine resin, an epoxy resin, and a vinyl chloride resin. Alternatively, the culture container 11 other than the portion through which light emitted from the light source 30 is transmitted may be formed of a material listed above or a metal material.

The environment controller 50 is configured to be capable of controlling, on the basis of the output of a control unit 61 described below, the temperature and humidity in the incubator 10, the gas introduced into the incubator 10, and the like, and adjusts the culture environment of the cell C.

The information processing apparatus 60 includes the control unit 61, the calculation unit 62, and a storage unit 63. The control unit 61 is a CPU that integrally controls the operation of the respective units of the detection apparatus 100. The control unit 61 in this embodiment is configured to be capable of controlling the light source 30, the detection unit 40, and the environment controller 50, and transmits control signals to them, which makes it possible to detect the change in the substrate in the culture solution B, which is changed in accordance with the change in the state of the cell C.

The calculation unit 62 calculates, on the basis of the electrical signal output from the detection unit 40, the intensity of the luminescence received by the detection unit 40. The calculation unit 62 outputs numerical data based on the digitized intensity of the luminescence to the storage unit 63 and the display unit 70.

The storage unit 63 includes a non-volatile storage medium such as a hard disk and a flash memory. The storage unit 63 stores the numerical data output from the calculation unit 62, measurement information of the detection apparatus 100, and the like. The measurement information is stored in the storage unit 63 in the state where, for example, identification information of the cell C of a detection target and the measurement data and time are associated with each other. Note that also the program to be executed by the control unit 61 is stored in the storage unit 63.

The information processing apparatus 60 includes hardware necessary for a computer such as a CPU (Central Processing Unit), a ROM (Read Only Memory), a RAM (Random Access Memory), and an HDD (Hard Disk Drive). The CPU (control unit 61) loads the program stored in the ROM or HDD (storage unit 63) into the RAM and executes the program, thereby controlling the operation of each of the detection unit 40, the environment controller 50, and the light source 30.

The program is installed in the information processing apparatus 60 via, for example, various storage media (internal memory). Alternatively, the program may be installed via the Internet or the like. In this embodiment, a PC (Personal Computer) or the like is used as the information processing apparatus 60, but another arbitrary computer may be used.

The display unit 70 displays the numerical data output from the calculation unit 62. The display unit 70 is, for example, a liquid crystal display, an organic EL (Electroluminescence) display, a plasma display, or the like.

Note that in this embodiment, the configuration of the detection apparatus 100 is not limited to the configuration example shown in FIG. 1. For example, the detection apparatus 100 may include an imaging unit that captures an image in the culture container 11, light emission of and the stack sensor 22, or the like, and a condensing unit such as a lens that guides luminescence emitted from the stack sensor 22 to the detection unit 40. Alternatively, the detection apparatus 100 may include an analysis unit that analyzes the state of the cell C on the basis of the numerical data output from the calculation unit 62.

[Configuration of Sensor Device]

APPLICATION EXAMPLE 1-1

FIG. 3 is an exploded perspective view showing a configuration example of the sensor device 20 according to this embodiment. As shown in the figure, the sensor device 20 includes the support substrate 21, a first sensor layer 221, and a second sensor layer 222.

As shown in FIG. 3, the support substrate 21 is a cylinder provided vertically below the stack sensor 22, and has a main surface 21*a* to be in contact with the culture container 11 and a main surface 21*b* to be in contact with the stack sensor 22. The support substrate 21 functions as a pedestal that supports the stack sensor 22.

A diameter D1 of the support substrate 21 is not particularly limited, and is, for example, not less than 1 mm and not more than 35 mm. Further, also a thickness D2 of the support substrate 21 is not particularly limited, and is, for example, not less than 10 nm and not more than 10 mm, typically, not less than 100 nm and not more than 10 µm. The size of the support substrate 21 is typically similar to that of the stack sensor 22. However, the support substrate 21 may be larger or smaller than the stack sensor 22 as long as the support substrate 21 is capable of supporting the stack sensor 22.

Further, the shape of the support substrate 21 is not limited to the cylinder as shown in FIG. 3. For example, the shape of the support substrate 21 may be a rectangular column, a triangular column, an elliptical column, or a polygonal column, and is not limited.

The material forming the support substrate 21 is typically glass, but is not limited thereto. The support substrate 21 is a transparent body through which light emitted from the light source 30 or luminescence of the stack sensor 22 is transmitted, which is formed of an inorganic material such as silicon, or an organic material such as a polystyrene resin, a polyethylene resin, a polypropylene resin, an ABS resin, nylon, an acrylic resin, a fluoropolymer, a polycarbonate resin, a polyurethane resin, a methylpentene resin, a phenolic resin, a melamine resin, an epoxy resin, and a vinyl chloride resin. Alternatively, the culture container 11 other than the portion through which light is transmitted may be formed of a material listed above or a metal material.

The first sensor layer 221 is a cylinder provided between the support substrate 21 and the second sensor layer 222, and has a main surface 221*a* to be in contact with the support substrate 21 and a main surface 221*b* to be in contact with the second sensor layer 222.

A diameter D3 of the first sensor layer 221 is not particularly limited, and is, for example, not less than 1 mm and not more than 35 mm. Further, also a thickness D4 of the first sensor layer 221 is not particularly limited, and is, for example, not less than 0.01 µm and not more than 10 µm. The size of the first sensor layer 221 is typically similar to those of the support substrate 21 and the second sensor layer 222. However, the present technology is not limited thereto, and the first sensor layer 221 may be larger or smaller than the support substrate 21 and the second sensor layer 222.

Further, the shape of the first sensor layer 221 is not limited to the cylinder as shown in FIG. 3. For example, the shape of the first sensor layer 221 may be a rectangular column, a triangular column, an elliptical column, or a polygonal column, and is not limited. The shape of the first sensor layer 221 may be the same as or different from those of the support substrate 21 and the second sensor layer 222.

The first sensor layer 221 is formed of a matrix material containing one or more types of first optically active substances that exhibit luminescence by excitation light. In this embodiment, in the case where a detection target of the first sensor layer 221 is oxygen in the culture solution B, the first optically active substance is, for example, a dye whose optical properties are changed by reacting with oxygen.

As an example of the above-mentioned dye, an arbitrary organic or inorganic substance is employed. Specific examples thereof include platinum porphyrin, a porphyrin derivative, a phthalocyanine derivative, an organometallic complex, pyrene, rhodamine, methylene blue, and a mixture thereof.

Further, as the matrix material forming the first sensor layer 221, a material having a sufficient transmittance of at least oxygen in the culture solution B is employed. As an example of such a matrix material, polystyrene, polypropylene, polycarbonate, polyethylene glycol, polyfluorinated ethylene, polyurethane, nylon, cellulose, polydimethylsiloxane, silicone rubber, butyl rubber, or the like is employed. Note that the matrix material forming the first sensor layer 221 is favorably a material having low solubility in the culture solution B.

The second sensor layer 222 is a cylinder provided on the first sensor layer 221, and has a main surface 222*a* to be in contact with the first sensor layer 221 and a main surface 222*b* to be adhered to (in contact with) the cell C.

A diameter D5 of the second sensor layer 222 is not particularly limited, and is, for example, not less than 1 mm and not more than 35 mm. Further, also a thickness D6 of the second sensor layer 222 is not limited, and is, for example, not less than 0.01 µm and not more than 10 µm. The size of the second sensor layer 222 is typically similar to those of the support substrate 21 and the first sensor layer 221. However, the present technology is not limited thereto, and the second sensor layer 222 may be larger or smaller than the support substrate 21 and the first sensor layer 221.

Further, the shape of the second sensor layer 222 is not limited to the cylinder as shown in FIG. 3. For example, the shape of the second sensor layer 222 may be a rectangular column, a triangular column, an elliptical column, or a polygonal column, and is not limited. The shape of the second sensor layer 222 may be the same as or different from those of the support substrate 21 and the first sensor layer 221.

The second sensor layer 222 is formed of a matrix material containing one or more types of second optically active substances that exhibit luminescence by excitation light. In this embodiment, in the case where a detection target of the second sensor layer 222 is a hydrogen ion in the culture solution B, the second optically active substance is, for example, a dye whose optical properties are changed by reacting with the hydrogen ion.

As a result, the second sensor layer 222 exhibits luminescence corresponding to the pH of the culture solution B by being irradiated with excitation light.

As an example of the above-mentioned dye, an arbitrary organic or inorganic substance is employed. Specific examples thereof include various conjugated compounds having a hydrogen ion acceptor group such as a hydroxyl group, a carboxylic acid group, a sulfonic acid group, and an amine group, e.g., fluorescein or bromothymol blue, and a mixture of the conjugated compound and another light emission compound.

Further, as the matrix material forming the second sensor layer 222, a material having a transmittance of the substrate to be a detection target of the first sensor layer 221 higher than that of the first sensor layer 221 is employed. For example, in the case where the detection target of the first sensor layer 221 is oxygen and the detection target of the second sensor layer 222 is a hydrogen ion, the second sensor layer 222 is formed of a matrix material having a transmittance of at least oxygen and a hydrogen ion.

Examples of the matrix material forming the second sensor layer 222 include siloxane gel, polyethylene glycol, polyvinyl alcohol, and polyalkylacrylamide.

Note that the second sensor layer 222 may be formed of a matrix material that is the same as or different from that of the first sensor layer 221 as long as the matrix material has a transmittance of the substrate to be a detection target of the first sensor layer 221 higher than that of the first sensor layer 221.

Further, in the case where the first sensor layer 221 is formed of a material having high solubility in the culture solution B, the matrix material forming the second sensor layer 222 is favorably a material having solubility in the culture solution B lower than that of the first sensor layer 221.

The stack sensor 22 according to this embodiment typically includes the two sensor layers, i.e., the first and second sensor layers 221 and 222. However, the present technology is not limited thereto, and the stack sensor 22 may have a multilayer structure in which three or more sensor layers are stacked. In this case, the stack sensor 22 has a multilayer structure in which sensor layers are stacked in the descending order of the transmittance of the substrate to be a detection target. That is, the sensor layer directly stacked on the support substrate 21 has the lowest transmittance of the substrate, and the uppermost sensor layer has the highest transmittance of the substrate.

APPLICATION EXAMPLE 1-2

Figure 4:
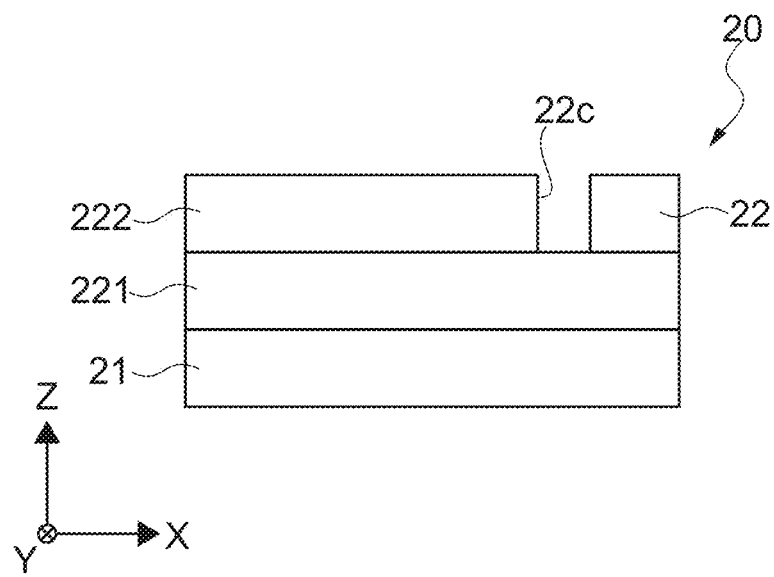
FIG. 4 is a schematic diagram showing another configuration example of the sensor device according to the above-mentioned embodiment.
Figure 5:
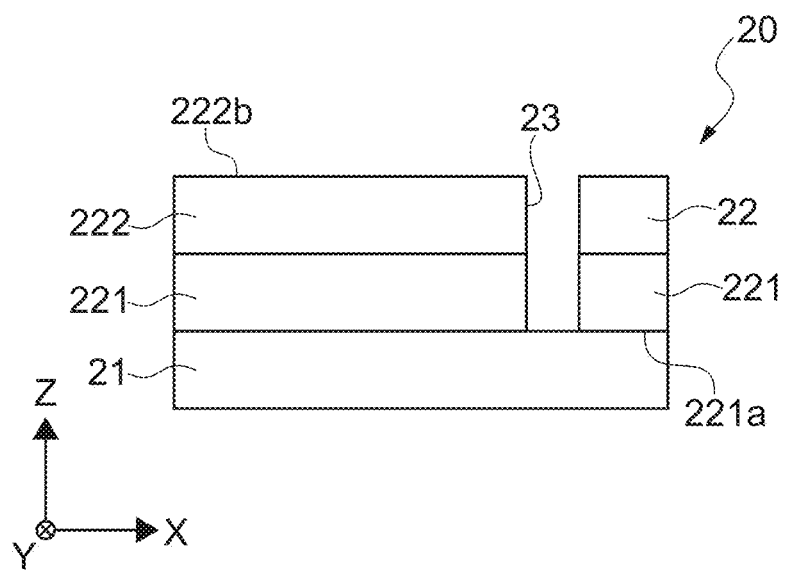
FIG. 5 is a schematic diagram showing another configuration example of the sensor device according to the above-mentioned embodiment.

FIG. 4 and FIG. 5 are each a schematic diagram showing another configuration example of the sensor device 20 according to this embodiment. In the sensor device 20, an opening 22c leading to the first sensor layer 221 may be provided in the second sensor layer 222 as shown in FIG. 4, or a passage portion 23 that communicates the main surface 221a of the first sensor layer 221 and the main surface 222b of the second sensor layer 222 with each other may be provided as shown in FIG. 5.

As a result, it is possible to form the stack sensor 22 in which the first and second sensor layers 221 and 222 are in a stacked relationship without depending on the transmittance of the substrate of the matrix materials forming the first and second sensor layers 221 and 222.

In the case of Application Example 1-2, for example, even in the case where the second sensor layer 222 has a transmittance of the substrate to be a detection target of the first sensor layer 221 lower than that of the first sensor layer 221, the substrate reaches the first sensor layer 221 via the opening 22c. Therefore, the first and the second sensor layers 221 and 222 are capable of individually detecting the substrate to be a detection target. That is, it is possible to detect, with the sensor device 20 alone, the changes in a plurality of substrates in the culture solution B in accordance with the change in the state of the cell C.

[Detection Method]

Next, an operation example of the detection apparatus 100 will be described.

Step 1: A control signal is transmitted from the control unit 61 to the light source 30, the detection unit 40, and the environment controller 50.

Step 2: The environment controller 50 controls the culture environment in the incubator 10.

Step 3: The light source 30 emits light and applies the light to the stack sensor 22. At this time, excitation light for exciting the optically active substance that has reacted with the substrate in the culture solution B is applied to the stack sensor 22.

Step 4: The stack sensor 22 containing the optically active substance exhibits luminescence. At this time, the stack sensor 22 exhibits luminescence corresponding to the change in the substrate in the culture solution B, which corresponds to the change in the state of the cell C.

Step 5: The detection unit 40 receives the luminescence in Step 4, and outputs the electrical signal corresponding to the intensity of the luminescence to the calculation unit 62.

Step 6: The calculation unit 62 calculates, on the basis of the electrical signal output from the detection unit 40, the intensity of the luminescence received by the detection unit 40, and the change in the intensity with time. Then, the calculation unit 62 outputs the numerical data based on the digitized intensity of the luminescence to the storage unit 63 and the display unit 70.

Step 7: The numerical data in Step 6 is stored in the storage unit 63, and displayed on the display unit 70.

Note that typically, the above-mentioned Steps 1 to 7 are executed in real time while culturing the cell C in this embodiment. However, the present technology is not limited thereto, and the above-mentioned Steps 1 to 7 may be executed after the culturing of the cell C is finished.

[Action]

The sensor device 100 according to this embodiment has a configuration in which the second sensor layer 222 is stacked on the first sensor layer 221. As a result, the sensor device 100 can be made compact, and it is possible to miniaturize and simplify the detection apparatus 100 including the sensor device 100.

Further, in the sensor device 20, the second sensor layer 222 is formed of a matrix material having a transmittance of the substrate to be a detection target of the first sensor layer 221 higher than that of the first sensor layer 221. As a result, even in the case of stacking the second sensor layer 222 on the first sensor layer 221, the substrate to be a detection target of the first sensor layer 221 can be transmitted through the second sensor layer 222 and can reach the first sensor layer 221.

Therefore, the sensor device 20 according to this embodiment can have a device configuration in which the first and second sensor layers 221 and 222 are in a stacked relationship, and the first and second sensor layers 221 and 222 are capable of individually detecting the substrate to be a detection target without impairing the measurement accuracy. That is, since it is possible to detect a plurality of substrates in the culture solution B with the sensor device 20, the spatial resolution of the sensor device 20 is improved.

Therefore, in accordance with the present technology, it is possible to provide the sensor device 20 that is capable of detecting a plurality of substrates in the culture solution B and has a compact device configuration due to the stacked structure of the stack sensor 22.

Further, in this embodiment, since the sensor device 20 has the stacked structure, the optically active substance contained in the first and second sensor layers 221 and 222 is less likely to be in contact with the culture solution B. Therefore, since the optically active substance is less likely to be invaded by the culture solution B, the deactivation of the optically active substance is suppressed. As a result, the durability of the sensor device 20 is improved.

In particular, in the case where the first sensor layer 221 is formed of, for example, a water-soluble matrix material having high solubility in the culture solution B, by configuring the stack sensor 22 such that the first sensor layer 221 is sandwiched between the support substrate 21 and the second sensor layer 222 having low solubility in the culture solution B, the first optically active substance contained in the first sensor layer 221 is prevented from being eluted in the culture solution B. As a result, the cell C is prevented from being damaged by the first optically active substance leaked into the culture solution B.

Second Embodiment

Figure 6:
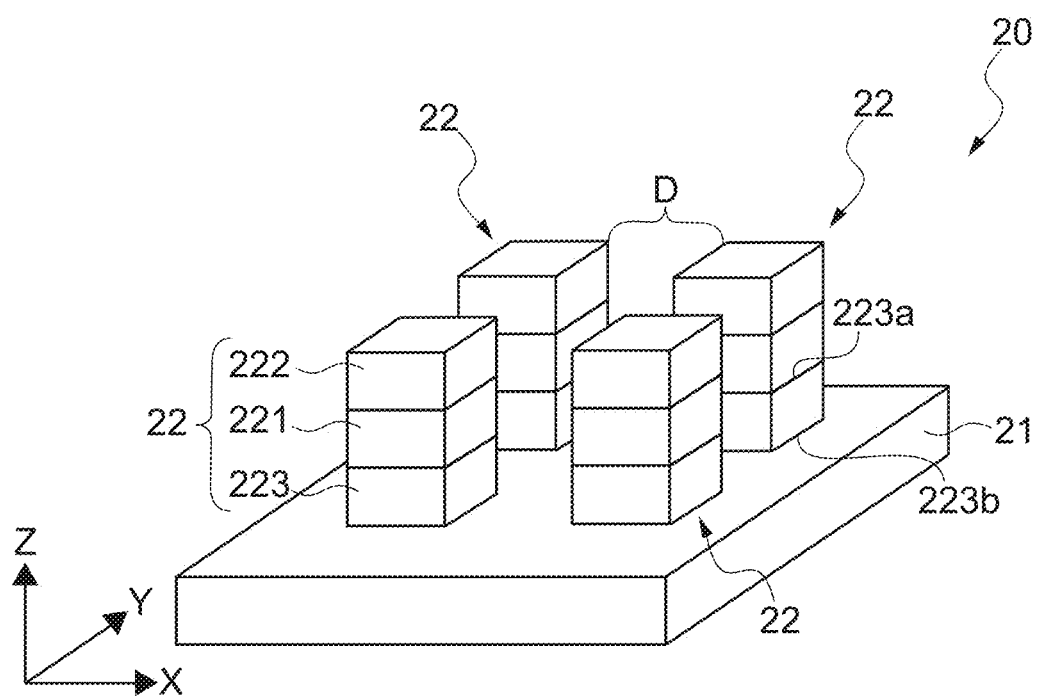
FIG. 6 is a schematic diagram showing a configuration example of a sensor device according to a second embodiment of the present technology.

FIG. 6 is a schematic diagram showing a configuration example of the sensor device 20 according to a second embodiment of the present technology. Hereinafter, similar configurations as those in the first embodiment will be denoted by similar reference symbols, and detailed description thereof will be omitted or simplified.

The sensor device 20 according to this embodiment is common to that in the first embodiment in that it includes the support substrate 21 and the first and second sensor layers 221 and 222. However, the sensor device 20 according to this embodiment is different from that in the first embodiment in that a plurality of stack sensors 22 each including them are provided at predetermined intervals on the support substrate 21.

APPLICATION EXAMPLE 2-1

As shown in FIG. 6, the sensor device 20 according to this embodiment further includes a third sensor layer 223 disposed on the support substrate 21 in alignment with the first and second sensor layers 221 and 222 in the Z axis direction.

The third sensor layer 223 is a rectangular column provided between the support substrate 21 and the first sensor layer 221, and has a main surface 223b to be in contact with the support substrate 21 and a main surface 223a to be in contact with the first sensor layer 221.

The size of the third sensor layer 223 is typically similar to those of the first and second sensor layers 221 and 222. However, the present technology is not limited thereto, and the third sensor layer 223 may be larger or smaller than the first and second sensor layers 221 and 222. The shape of the third sensor layer 22 is not limited to the rectangular column as shown in FIG. 6. For example, the shape of the third sensor layer 22 may be a triangular column, a cylinder, an elliptical column, or a polygonal column, and is not limited. Further, the shape of the third sensor layer 223 may be the same as or different from those of the first and second sensor layers 221 and 222.

The third sensor layer 223 is formed of a matrix material containing one or more types of third optically active substances that exhibit luminescence by excitation light. The third optically active substance is, for example, a dye whose optical properties are changed by reacting with an arbitrary substrate in the culture solution B. The substrate may be, for example, the substrates exemplified in the above-mentioned first embodiment or different from these substrates.

Further, as an example of the third optically active substance that reacts with such a substrate, any of the dyes exemplified in the above-mentioned first embodiment may be used, or a dye different from these dyes may be used.

Further, as the matrix material forming the third sensor layer 223, a material having a transmittance of a substrate in the culture solution B is employed. As such a matrix material, the matrix materials exemplified in the above-mentioned first embodiment may be used, or a matrix different from these matrix materials may be used.

A plurality of stack sensors 22 according to this embodiment is provided at predetermined intervals D on the support substrate 21. As a result, since a substrate to be a detection target of each of the first to third sensor layers 221, 222, and 223 can respectively reach the first to third sensor layers 221, 222, and 223 via the intervals D, it is possible to configure the stack sensor 22 in which the sensor layers 221, 222, and 223 are in a stacked relationship without depending on the transmittance of the substrate of the matrix material forming each of the sensor layers 221, 222, and 223. Therefore, the operation and effect similar to those in the above-mentioned Application Example 1-2 can be achieved.

APPLICATION EXAMPLE 2-2

Figure 7:
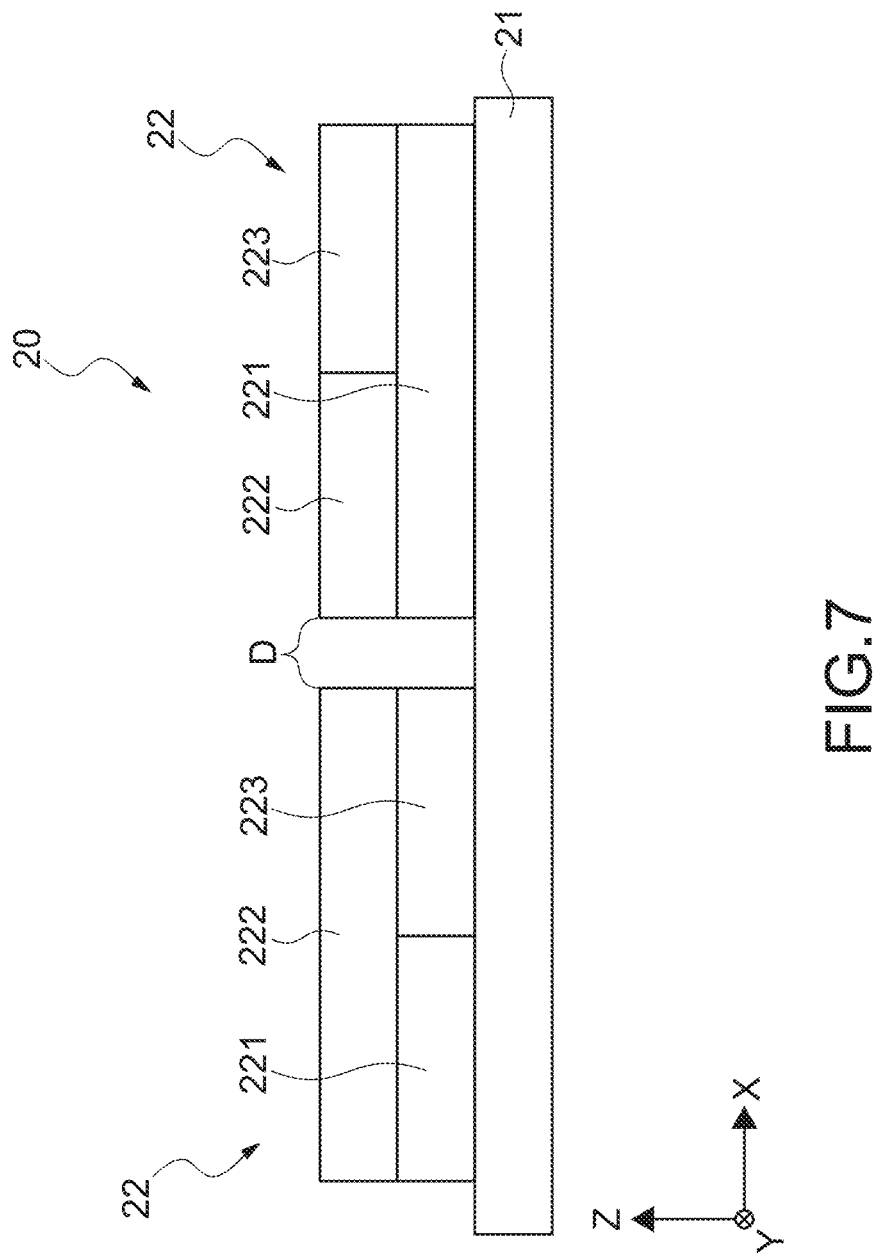
FIG. 7 is a schematic diagram showing another configuration example of the sensor device according to the above-mentioned embodiment.

FIG. 7 is a schematic diagram showing another configuration example of the sensor device 20 according to this embodiment. As shown in FIG. 7, the sensor device 20 according to this embodiment may have a configuration in which the stack sensors 22 are disposed at the predetermined intervals D on the support substrate 21 and the third sensor layer 223 is aligned with the first sensor layer 221 or the second sensor layer 222 in the XY plane direction. As a result, similar operation and effect can be achieved for the similar reason as that in the Application Example 2-1.

EXAMPLE

Hereinafter, Example of the present technology will be described. Note that the present technology is not limited to the following Example.

[Preparation of Stack Sensor Substrate]

The stack sensor substrate (see FIG. 3) described in the above-mentioned embodiment was prepared in the following procedure.

First, a support substrate formed of glass was prepared, and a polystyrene layer containing platinum porphyrin that reacts with oxygen was prepared. Subsequently, a stack sensor substrate having a diameter of 15 mm and a thickness of 1 μm was prepared by depositing a siloxane gel layer containing fluorescein that reacts to pH (hydrogen ion) on the polystyrene layer.

[Evaluation of Light Emission Behavior]

Figure 8:
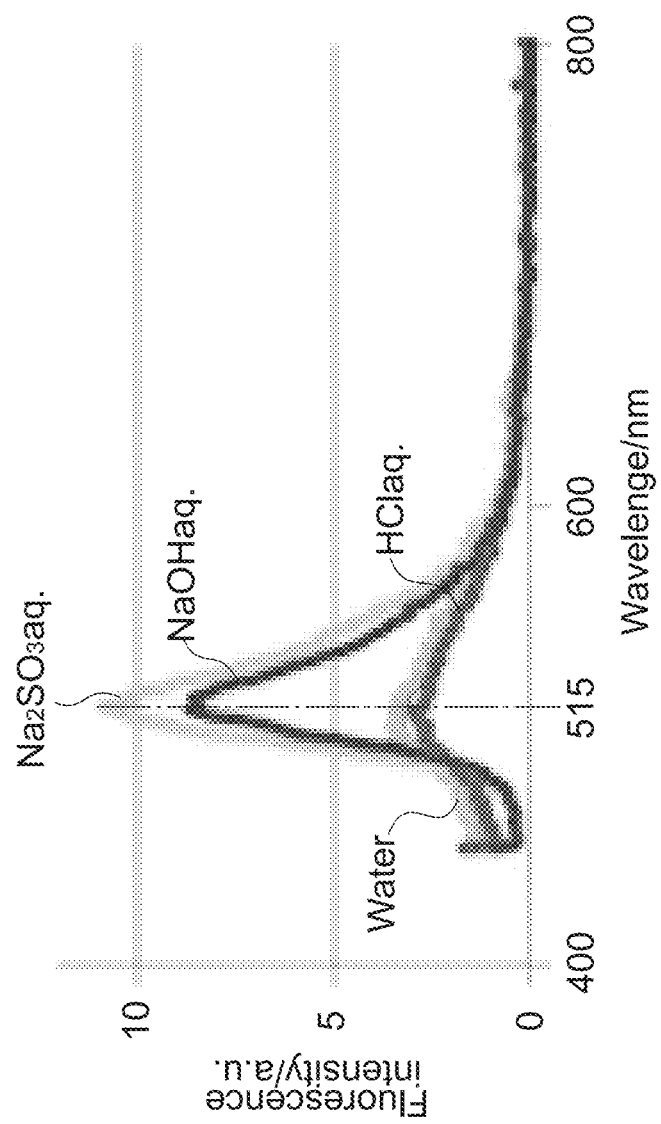
FIG. 8 is a graph summarizing results of evaluating the light emission behavior of a sensor device according to an Example of the present technology.

Next, the reactivity to oxygen and pH of the stack sensor substrate thus obtained was evaluated. Specifically, the fluorescence intensity in the case where the stack sensor substrate was immersed in each of aqueous solutions, i.e., pure water, a saturated sodium sulfate aqueous solution (pH 11 or more), a 0.01 hydrochloric acid aqueous solution (pH 2), and 0.01 M sodium hydroxide aqueous solution (pH 11), was measured. At this time, excitation light having an excitation wavelength of 430 nm was applied to the stack sensor substrate. FIG. 8 is a graph summarizing the results.

Referring to FIG. 8, it can be seen that the fluorescence intensity at the wavelength of 515 nm increases as the pH of each solution increases. This matches the general fluorescence intensity of fluorescein.

Figure 9:
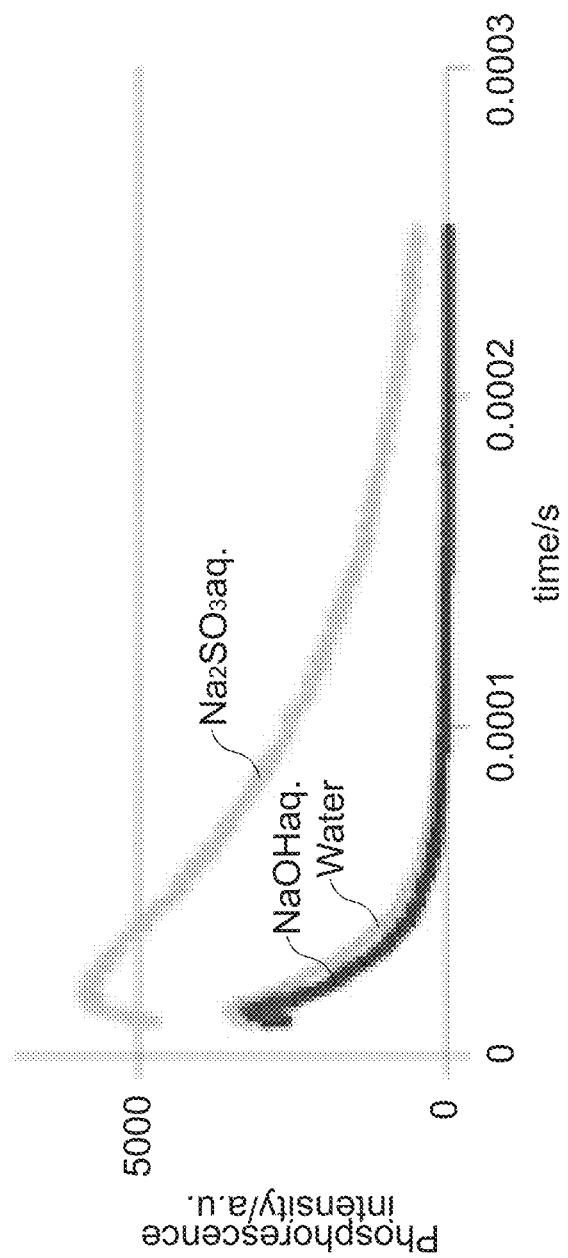
FIG. 9 is a graph summarizing results of evaluating the light emission behavior of the sensor device according to the above-mentioned Example.

Subsequently, the phosphorescence lifetime in the case where the stack sensor substrate was immersed in each of aqueous solutions, i.e., pure water, a saturated sodium sulfate aqueous solution, and 0.01 M sodium hydroxide aqueous solution, was measured. At this time, excitation light having an excitation wavelength of 370 nm with the measurement wavelength of 650 nm was applied to the stack sensor substrate. FIG. 9 is a graph summarizing the results.

Referring to FIG. 9, it can be seen that the phosphorescence lifetime increases only in the case where the stack sensor substrate was immersed in the saturated sodium sulfate aqueous solution.

It is known that the phosphorescence life time of platinum porphyrin generally increases in an environment with a low oxygen concentration. Here, in an aqueous solution containing sodium nitrite as a solute, the sodium nitrite functions as an oxygen quencher, so that the oxygen concentration in the aqueous solution is significantly reduced.

That is, the graph shown in FIG. 9 matches the general phosphorescence lifetime of platinum porphyrin in an aqueous solution with a low oxygen concentration, and shows that the siloxane gel layer corresponds to the oxygen concentration in the aqueous solution.

From these results, it was experimentally confirmed that in the sensor device 20 according to the above-mentioned embodiment, the sensors layers 221 and 222 were individually capable of reacting to the substrate in the culture solution B. That is, it was confirmed that the sensor device 20 could have a configuration in which the sensor layers 221 and 222 were stacked.

[Cell Culture Experiment]

Figure 10:
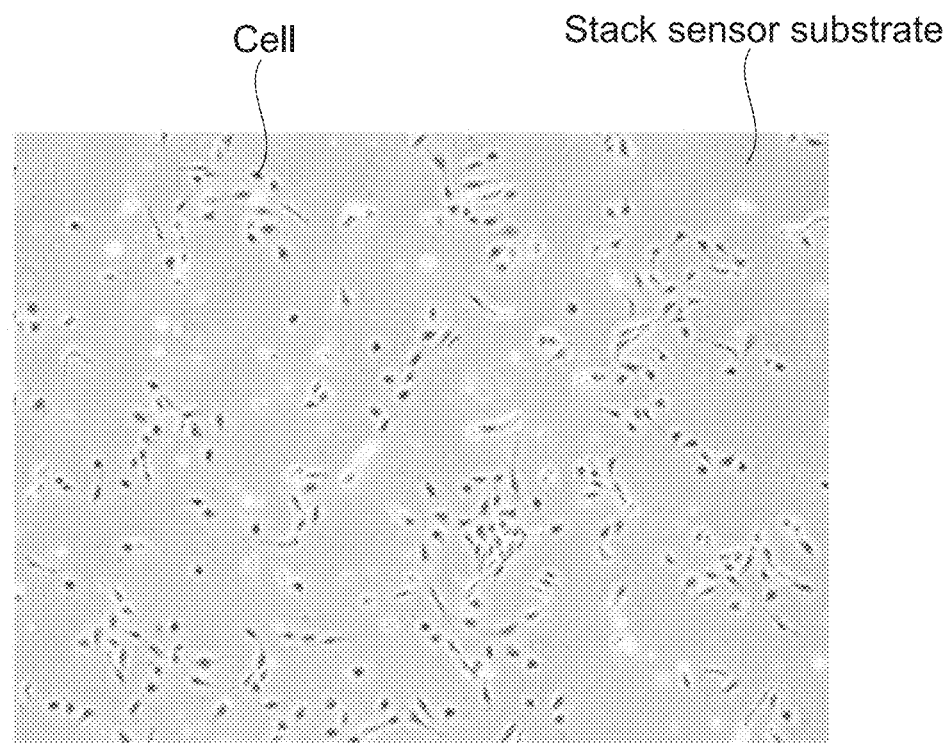
FIG. 10 is an image obtained by imaging cells cultured on a stack sensor substrate in the above-mentioned Example.

Next, a cell culture experiment was performed using the stack sensor substrate obtained by the above-mentioned method. The culture conditions were as follows. FIG. 10 is a diagram showing an image obtained by seeding cells and imaging, with an optical microscope, the cells after being cultured on the stack sensor substrate in the incubator for 18 hours.

Culture Conditions
Cell: HUVEC cell
Culture container: polystyrene 35 mmφ dish
Culture solution: EGM-2
Seeding number: $2.5 \times 10^4$ cell/mL×2 mL Referring to FIG. 10, it can be seen that the cells stretches the scaffold and adheres to the stack sensor substrate. From this result, it was experimentally confirmed that cells could be cultured on the stack sensor substrate.

Although embodiments of the present technology have been described above, it goes without saying that the present technology is not limited to the above-mentioned embodiments and various modifications can be made.

Figure 11:
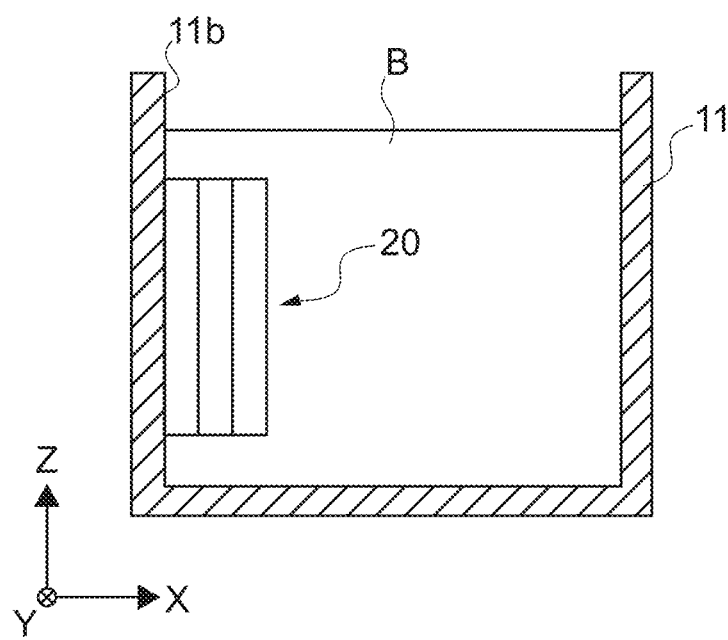
FIG. 11 is a schematic diagram showing a configuration example of a sensor device according to a modified example of the present technology.
Figure 12:
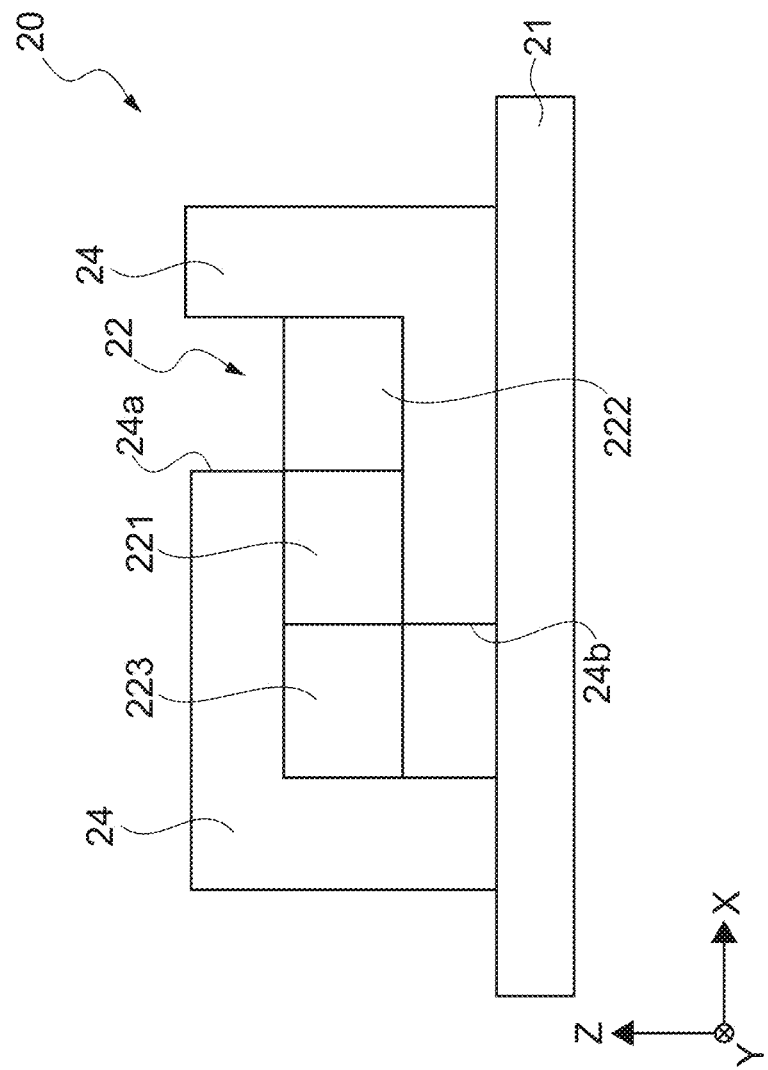
FIG. 12 is a schematic diagram showing a configuration example of the sensor device according to the above-mentioned modified example.

FIG. 11 and FIG. 12 are each a schematic diagram showing a configuration example of the sensor device 20 according to a modified example of the present technology. For example, the sensor device 20 does not necessarily need to be disposed on the bottom surface 11a of the culture container 11, and may be disposed on an inner wall surface (side surface) 11b of the culture container 11 as shown in FIG. 11.

Alternatively, as shown in FIG. 12, the sensor device 20 may be disposed on the support substrate 21 and supported by a light reflection portion 24 having a refractive index higher than that of the stack sensor 22. In this case, the light that has entered the stack sensor 22 passes from an incident portion 24a to an emission portion 24b while being totally reflected.

Further, the sensor device 20 according to the above-mentioned embodiments includes the support substrate 21 and the stack sensor 22. However, the present technology is not limited thereto, and the sensor device 20 may further include a layer that imparts functionality to the stack sensor 22. Specifically, the stack sensor 22 may be coated with a biocompatible substance or a substance capable of adsorbing and desorbing the cell C. Alternatively, the stack sensor 22 may be coated with a cell recognition substance such as an antibody and protein.

Further, the sensor device 20 according to the above-mentioned embodiments is typically used while being immersed in the culture solution B in the culture container 11. However, the present technology is not limited thereto, and the sensor device 20 may be embedded in, for example, a microchannel chip and used. It can be used for any purpose.

In addition, also the method of preparing the first and second sensor layers 221 and 222 constituting the sensor device 20 is not particularly limited. For example, insolubilization treatment such as cross-linking treatment may be performed on each of the sensor layers 221 and 222, or the first and second sensor layers 221 and 222 may be prepared by an electrospray method, an injection molding method, or the like.

Further, the detection apparatus 100 according to the present technology may be used for biological evaluation of those other than a cell such as a tissue, a sperm, a fertilized egg, and a microorganism. Further, the present technology is applicable also to an arbitrary cell such as a biological sample taken from a living body, e.g., an unfertilized egg cell (egg) or embryo of a living organism in the field of livestock or the like, or a stem cell, an immune cell, a cancer cell or the like in the field of regenerative medicine, pathology, or the like.

In addition, in the present specification, "a change in a substrate according to a change in the state of the cell" conceptually includes all environmental changes such as a change in the concentration of a substrate in a culture solution, a change in optical properties, and a change in a light emission mode, which occur due to the metabolic activity of the cell.

Further, in the present specification, "reaction between a substrate and an optically active substance" conceptually includes all chemical reactions such as binding, coordination, and trapping that change, by the reaction of the optically active substance with the substrate, the structural formula from that before the reaction to the different one.

It should be noted that the present technology may take the following configurations.

(1) A sensor device, including:
a stack sensor that includes
a first sensor layer that has, as a detection target, a first substrate in a culture solution, the first substrate being changed in accordance with a change in a state of a cell, and
a second sensor layer that has, as a detection target, a second substrate in the culture solution and is provided on the first sensor layer, the second substrate being changed in accordance with the change in the state.

(2) The sensor device according to (1) above, in which
the first sensor layer contains a first optically active substance that reacts with the first substrate, and
the second sensor layer contains a second optically active substance that reacts with the second substrate and has a first main surface to be in contact with the first sensor layer and a second main surface to be in contact with the cell.

(3) The sensor device according to (1) or (2) above, in which
the second sensor layer has a transmittance of the first substrate higher than that of the first sensor layer.

(4) The sensor device according to any one of (1) to (3) above, in which
the second sensor layer has an opening leading to the first sensor layer.

(5) The sensor device according to any one of (1) to (4) above, in which
the first sensor layer contains a first optically active substance that reacts with oxygen being the first substrate, and
the second sensor layer contains a second optically active substance that reacts with a hydrogen ion being the second substrate.

(6) The sensor device according to any one of (2) to (5) above, in which
the first sensor layer contains platinum porphyrin as the first optically active substance, and
the second sensor layer contains fluorescein as the second optically active substance.

(7) The sensor device according to any one of (1) to (6) above, further including
a support substrate that supports the stack sensor.

(8) The sensor device according to (7) above, in which
the first sensor layer has a third main surface to be in contact with the support substrate and a fourth main surface to be in contact with the second sensor layer, and has solubility in the culture solution higher than that of the second sensor layer.

(9) The sensor device according to (7) or (8) above, in which
the stack sensor includes a plurality of stack sensors provided the support substrate at predetermined intervals.

(10) The sensor device according to any one of (1) to (9) above, further including
a third sensor layer that is aligned with the first sensor layer.

(11) A detection apparatus, including:
a sensor device that includes a stack sensor and is disposed on an inner surface of a culture container, the stack sensor including a first sensor layer that has, as a detection target, a first substrate in a culture solution, the first substrate being changed in accordance with a change in a state of a cell, and a second sensor layer that has, as a detection target, a second substrate in the culture solution and is provided on the first sensor layer, the second substrate being changed in accordance with the change in the state;
a light source that applies light to the stack sensor; and
a detection unit that detects light that has been transmitted through the stack sensor.

REFERENCE SIGNS LIST

100 detection apparatus
10 incubator
11 culture container
20 sensor device
21 support substrate
22 stack sensor
30 light source
40 detection unit
50 environment controller
60 information processing apparatus
70 display unit
221 first sensor layer
222 second sensor layer

The invention claimed is:

1. A sensor device, comprising:
a plurality of stack sensors provided on a support substrate at predetermined intervals, wherein the plurality of stack sensors include:
a first sensor layer that has, as a first detection target, a first substrate in a culture solution, the first substrate being changed in accordance with a change in a state of a cell,
a second sensor layer that has, as a second detection target, a second substrate in the culture solution, the second substrate being changed in accordance with the change in the state of the cell, and
a third sensor layer that has, as a third detection target, a third substrate in the culture solution, the third substrate being changed in accordance with the change in the state of the cell, and
wherein the plurality of stack sensors include:
a first stack sensor with the first sensor layer and the third sensor layer adjacent to each other and aligned in a first XY direction, with the second sensor layer provided across both of the first sensor layer and the third sensor layer, and
a second stack sensor with the second sensor layer and the third sensor layer adjacent to each other and aligned in the first XY direction, with both the second sensor layer and the third sensor layer provided across the first sensor layer.

2. The sensor device according to claim 1, wherein
the first sensor layer contains a first optically active substance that reacts with the first substrate,
the second sensor layer contains a second optically active substance that reacts with the second substrate, and
the third sensor layer contains a third optically active substance that reacts with the third substrate.

3. The sensor device according to claim 2, wherein
the first sensor layer contains the first optically active substance that reacts with oxygen being the first substrate,
the second sensor layer contains the second optically active substance that reacts with a hydrogen ion being the second substrate, and
the third sensor layer contains the third optically active substance that reacts with the third substrate that is different than the first substrate and the second substrate.

4. The sensor device according to claim 3, wherein
the first sensor layer contains platinum porphyrin as the first optically active substance, and
the second sensor layer contains fluorescein as the second optically active substance.

5. A detection apparatus, comprising a sensor device according to claim 1;
a light source that applies light to the plurality of stack sensors; and
a detection unit that detects light that has been transmitted through the plurality of stack sensors.

* * * * *